United States Patent

Sayo et al.

[11] Patent Number: 5,808,162
[45] Date of Patent: Sep. 15, 1998

[54] CHIRAL UNSYMMETRIC DIPHOSPHINE COMPOUND AND TRANSITION METAL COMPLEX CONTAINING THE SAME AS LIGAND

[75] Inventors: Noboru Sayo; Xiaoyong Zhang; Tatsuya Omoto; Tohru Yokozawa; Tetsuro Yamasaki; Hidenori Kumobayashi, all of Kanagawa, Japan

[73] Assignee: Takasago International Corporation, Tokyo, Japan

[21] Appl. No.: 683,199

[22] Filed: Jul. 18, 1996

[30] Foreign Application Priority Data

Jul. 21, 1995  [JP]  Japan .................... 7-206696

[51] Int. Cl.⁶ .................... C07F 5/02; C07F 9/06; C07F 9/28; C07D 327/00
[52] U.S. Cl. .................... 568/10; 568/17; 546/22; 549/5; 549/6; 549/220
[58] Field of Search .................... 568/17, 10, 13; 556/13, 20; 514/107, 184, 186, 187, 188, 75, 82, 95, 96, 99, 100; 546/2, 21, 22; 549/3, 5, 6, 220

[56] References Cited

U.S. PATENT DOCUMENTS

| | | | |
|---|---|---|---|
| 4,556,740 | 12/1985 | Hansen et al. | 568/13 |
| 5,021,593 | 6/1991 | Nohira et al. | 556/20 |
| 5,223,632 | 6/1993 | Ishizaki et al. | 556/21 |
| 5,274,125 | 12/1993 | Broger et al. | 549/216 |
| 5,306,834 | 4/1994 | Takaya et al. | 549/263 |
| 5,430,191 | 7/1995 | Foricher et al. | 568/12 |
| 5,457,219 | 10/1995 | Foricher et al. | 556/404 |
| 5,508,438 | 4/1996 | Broger et al. | 549/6 |
| 5,514,805 | 5/1996 | Broger et al. | 546/176 |

FOREIGN PATENT DOCUMENTS

| | | |
|---|---|---|
| 0553778 | 1/1993 | European Pat. Off. . |
| 9315089 | 5/1993 | WIPO . |

*Primary Examiner*—Deborah C. Lambkin
*Attorney, Agent, or Firm*—Sughrue, Mion, Zinn, Macpeak & Seas, PLLC

[57] ABSTRACT

A novel chiral unsymmetric diphosphine compound of formula (I):

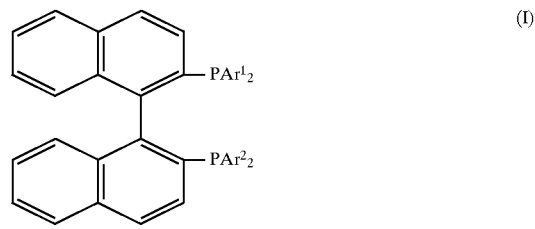

wherein $Ar^1$ and $Ar^2$, which are different from each other, each represent a substituted or unsubstituted phenyl group, a substituted or unsubstituted naphthyl group, a pyridyl group, a quinolyl group, an isoquinolyl group, a furfuryl group, a benzofurfuryl group, a thienyl group, or a benzothienyl group, and a transition metal complex containing the diphosphine compound as a ligand. The complex catalyzes various asymmetric synthesis reactions, e.g., asymmetric hydrogenation or asymmetric hydrosilylation, exhibiting excellent performance in selectivity, conversion and catalytic activity, to provide a product of desired absolute configuration at high optical purity and in high yield.

2 Claims, No Drawings

CHIRAL UNSYMMETRIC DIPHOSPHINE COMPOUND AND TRANSITION METAL COMPLEX CONTAINING THE SAME AS LIGAND

FIELD OF THE INVENTION

This invention relates to a novel chiral unsymmetric diphosphine compound, an intermediate therefor, a process for preparing the intermediate and the diphosphine compound, and a transition metal complex containing the diphosphine compound as a ligand.

BACKGROUND OF THE INVENTION

Many transition metal complexes have been used as a catalyst for asymmetric synthesis, such as asymmetric hydrogenation, asymmetric isomerization, and asymmetric hydrosilylation, and a good number of reports have been made on such transition metal complex catalysts.

Many complexes exhibiting excellent performance in catalytic asymmetric synthesis are found among those comprising a transition metal, e.g., rhodium, ruthenium, iridium, palladium or nickel, and an optically active tertiary phosphine compound as a ligand. To further improve the performance of these catalysts, various phosphine compounds having a unique structure have been developed to date as disclosed, e.g., in Nippon Kagakukai (ed.), *KAGAKU SOSETSU*, Vol. 32, pp. 237–238, "YUKI KINZOKU SAKUTAI NO KAGAKU" (1982) and Ryoji Noyori, *Asymmetric Catalysis in Organic Synthesis*, A Wiley-Interscience Publication.

In particular, 2,2'-bis(diphenylphosphino)-1,1'-binaphthyl (hereinafter abbreviated as BINAP) is one of excellent phosphine ligands, and a rhodium complex and a ruthenium complex using BINAP as a ligand have been reported in JP-A-55-61937 and JP-A-61-63690 (the term "JP-A" as used herein means an "unexamined published Japanese patent application"). JP-A-60-199898 and JP-A-61-63690 report that a rhodium or ruthenium complex using 2,2'-bis[di(p-tolyl)phosphino]-1,1'-binaphthyl as a ligand brings satisfactory reaction results in asymmetric hydrogenation and asymmetric isomerization. JP-A-3-255090 declares that a ruthenium complex having 2,2'-bis[di(3,5-dialkylphenyl)phosphino]-1,1'-binaphthyl gives good results in asymmetric hydrogenation of β-keto esters.

The above-mentioned phosphine compounds can be prepared by, for example, a process comprising bromination of a racemic binaphthol compound with triphenylphosphine dibromide at a high temperature (e.g., 240° to 320° C.), forming a Grignard reagent and condensation of the Grignard reagent with a diarylphosphinyl chloride to obtain a phosphine dioxide compound, optically resolving the phosphine dioxide compound, and reducing the resulting optically active compound with a reducing agent, e.g., trichlorosilane to obtain a tertiary phosphine compound (BINAP derivative) (see *J. Org. Chem.*, Vol. 51, p. 629 (1986)). BINAP can also be synthesized by preparing 2,2'-bis(trifluoromethanesulfonyloxy)-1,1'-binaphthyl from optically active binaphthol and reacting the compound with diphenyl phosphine in the presence of a nickel-phosphine complex as described in *J. Org. Chem.*, Vol. 59, pp. 7180–7181 (1994).

In recent years, a ligand having a binaphthyl skeleton and yet having an unsymmetric structure with no $C_2$ chirality due to the different substituents on the 2- and 2'-positions has been synthesized, and transition metal complexes using this ligand have been reported (see *J. Am. Chem. Soc.*, Vol. 115, p. 7033 (1993) and JP-A-6-263776). For example, 2-(diphenylphosphino)-1,1'-binaphthalen-2'-yl-(1,1'-binaphthalen-2,2'-yl)phosphite was found to exhibit excellent performance in asymmetric hydroformylation of olefins.

However, compounds having an optically pure binaphthyl skeleton generally meet difficulty in modifying with a functional group as compared with those derived from optically pure tartaric acid or amino acid. There are only a few reports on synthesis of that kind of derivatives or ligands having an unsymmetric structure.

When used in asymmetric synthesis, a transition metal complex having, as a ligand, a known symmetric phosphine compound, such as BINAP, is often unsatisfactory in selectivity (chemoselectivity and enantioselectivity), conversion, catalytic activity, and optical purity for some reactions or some reaction substrates. Therefore, it has been keenly demanded in the art to develop an optically active phosphine compound capable of a new catalytic asymmetric synthesis reaction or different asymmetric recognition for the sake of utility of chiral compounds and also to develop unsymmetric phosphine ligands that could be expected to be different from conventional phosphine compounds in selectivity (chemoselectivity and enantioselectivity), conversion, catalytic activity, and optical purity.

SUMMARY OF THE INVENTION

An object of the invention is to provide a novel unsymmetric diphosphine compound meeting the above demand.

Another object of the invention is to provide a novel unsymmetric diphosphine monoxide compound which is an intermediate for preparing the above-described unsymmetric diphosphine compound.

A further object of the invention is to provide a process for preparing the above-described unsymmetric diphosphine compound and its intermediate, unsymmetric diphosphine monoxide compound.

A still further object of the invention is to provide a novel transition metal-unsymmetric diphosphine complex comprising a transition metal, e.g., ruthenium, rhodium, iridium, palladium or nickel, and the above-described unsymmetric diphosphine compound as a ligand, which complex is a promising catalyst for various asymmetric synthesis reactions.

In the course of study on a ligand capable of catalytic asymmetric reactions, the inventors have succeeded in synthesis of a novel unsymmetric diphosphine compound having a binaphthyl skeleton and yet having no $C_2$ chirality and found the compound capable of forming a complex with a transition metal. Based on this finding and as a result of further study, the inventors have reached the present invention.

The invention relates, in its first aspect, to an unsymmetric diphosphine compound represented by formula (I):

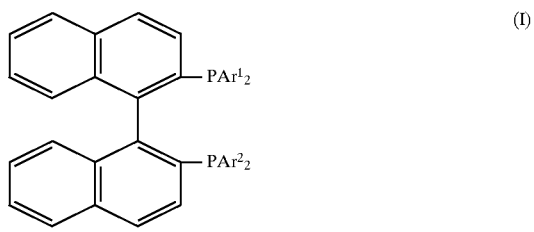

wherein $Ar^1$ and $Ar^2$, which are different from each other, each represent a phenyl group, a phenyl group substituted with 1 to 5 groups arbitrarily selected from the group consisting of a halogen atom, a lower alkyl group, a lower alkoxy group, a di(lower alkyl)amino group, a halogenated lower alkyl group, and a phenyl group, a naphthyl group, a naphthyl group substituted with a lower alkyl group or a lower alkoxy group, a pyridyl group, a quinolyl group, an isoquinolyl group, a furfuryl group, a benzofurfuryl group, a thienyl group, or a benzothienyl group.

The invention relates, in its second aspect, to an unsymmetric diphosphine monoxide compound represented by formula (II):

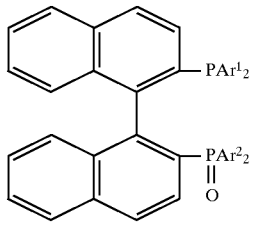

wherein $Ar^1$ and $Ar^2$, which are different from each other, have the same meaning as defined above, which is an intermediate for preparing the unsymmetric diphosphine compound (I).

The invention relates, in its third aspect, to a process for preparing the unsymmetric diphosphine compound (I) comprising reacting a 2-disubstituted phosphino-2'-trifluoromethanesulfonyloxy-1,1'-binaphthyl represented by formula (III):

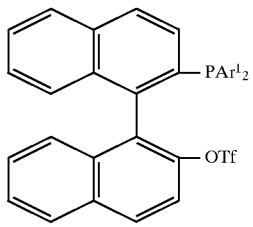

wherein $Ar^1$ is as defined above; and Tf represents a trifluoromethanesulfonyl group, with a disubstituted phosphine oxide represented by formula (IV):

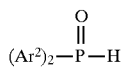

wherein $Ar^2$ is as defined above, provided that it is different from $Ar^1$, in the presence of a transition metal-phosphine complex to form an unsymmetric diphosphine monoxide compound (II), and reducing the compound (II).

The invention relates, in its fourth aspect, to a transition metal-unsymmetric diphosphine complex, in which the transition metal is selected from rhodium, ruthenium, iridium, palladium, and nickel, and the unsymmetric diphosphine is the unsymmetric diphosphine compound (I).

Both the unsymmetric diphosphine compound (I) and the unsymmetric diphosphine monoxide compound (II) embrace the (−)-form and the (+)-form, and all these isomers are included under the scope of the invention.

DETAILED DESCRIPTION OF THE INVENTION

The unsymmetric diphosphine compound (I) and the unsymmetric diphosphine monoxide compound (II) are both novel compounds.

In formulae (I) and (II), $Ar^1$ and $Ar^2$ each represent a substituted or unsubstituted phenyl group, a substituted or unsubstituted naphthyl group, a pyridyl group, a quinolyl group, an isoquinolyl group, a furfuryl group, a benzofurfuryl group, a thienyl group, or a benzothienyl group. Specific examples of the substituted phenyl group are p-tolyl, p-methoxyphenyl, p-trifluoromethylphenyl, p-fluorophenyl, p-dimethylaminophenyl, p-t-butylphenyl, 3,5-dimethylphenyl, 3,5-di-t-butylphenyl, 3,4,5-trimethoxyphenyl, 3,5-dimethyl-4-methoxyphenyl, 3,5-ditrifluoromethylphenyl, 3,5-dichlorophenyl, pentafluorophenyl, and biphenyl. The substituted or unsubstituted naphthyl group includes α-naphthyl, β-naphthyl, 6-methoxy-α-naphthyl, and 6-methoxy-β-naphthyl. The pyridyl group includes 2-pyridyl, 3-pyridyl, and 4-pyridyl. The quinolyl group includes 2-quinolyl, 3-quinolyl, and 4-quinolyl. The isoquinolyl group includes 1-isoquinolyl, 3-isoquinolyl, and 4-isoquinolyl. The furfuryl group includes 2-furfuryl and 3-furfuryl. The benzofurfuryl group includes 2-benzofurfuryl and 3-benzofurfuryl. The thienyl group includes 2-thienyl and 3-thienyl. The benzothienyl group includes 2-benzothienyl and 3-benzothienyl. The substituents $Ar^1$ and $Ar^2$ are arbitrarily combined with no particular limitation as far as they are different from each other.

Unless otherwise specified, the term "lower alkyl group" is intended to include methyl, ethyl, n-propyl, isopropyl, n-butyl, isobutyl, sec-butyl, and t-butyl groups; the term "lower alkoxy group" is intended to include methoxy, ethoxy, n-propoxy, isopropoxy, n-butoxy, isobutoxy, sec-butoxy, and t-butoxy groups; the term "halogen atom" includes fluorine, chlorine and bromine; the term "halogenated lower alkyl group" includes trifluoromethyl and trichloromethyl groups; and the term "di(lower alkyl)amino group" includes a dimethylamino group. That is, the "lower" alkyl or alkoxy means alkyl or alkoxy having 1 to 4 carbon atoms.

The 2-disubstituted phosphino-2'-trifluoromethanesulfonyloxy-1,1'-binaphthyl (III), which is a starting material used in the invention, can easily be synthesized from a known compound, 1,1'-bi-2-naphthol, in accordance with the following reaction scheme A.

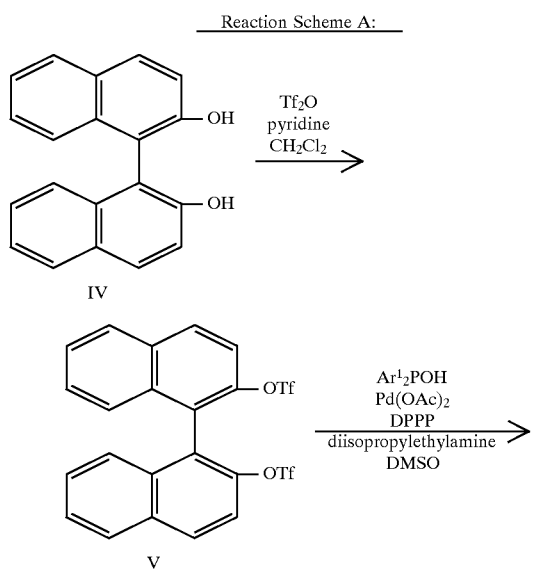

-continued
Reaction Scheme A:

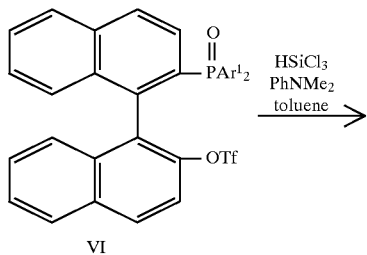

Reaction Scheme B:

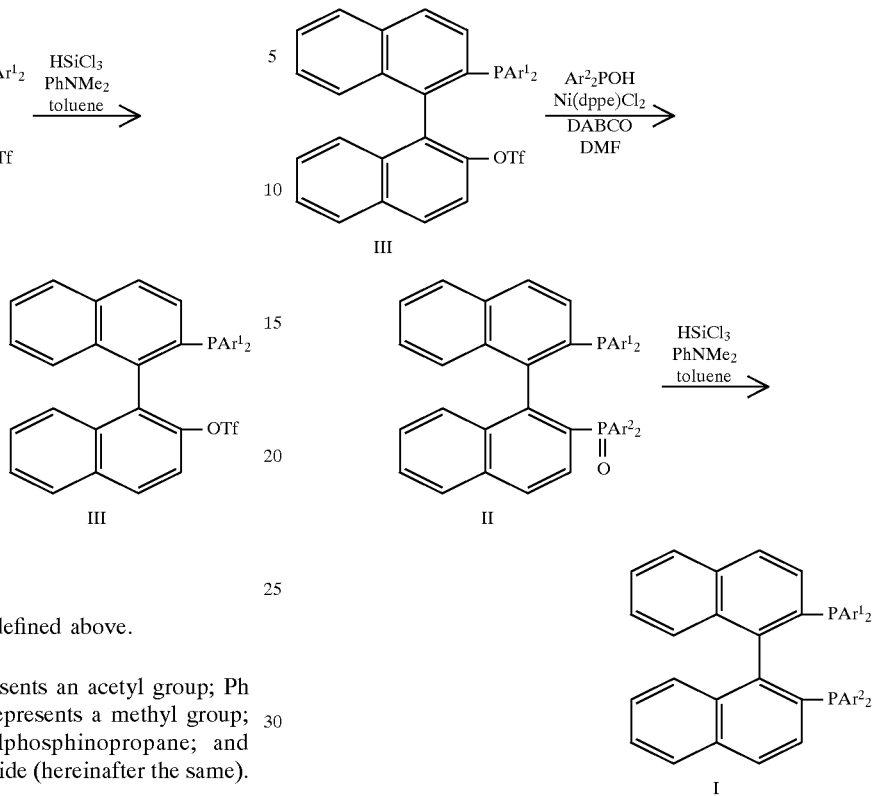

wherein Ar¹, Ar², and Tf are as defined above.

In the above scheme, Ac represents an acetyl group; Ph represents a phenyl group; Me represents a methyl group; DPPP represents 1,3-bisphenylphosphinopropane; and DMSO stands for dimethyl sulfoxide (hereinafter the same).

That is, optically active 1,1'-bi-2-naphthol (IV) is reacted with trifluoromethanesulfonic acid anhydride ($Tf_2O$) to obtain 2,2'-bis(trifluoromethanesulfonyloxy)-1,1'-binaphthyl (V) in accordance with the method described in Tetrahedron Letters, Vol. 31, pp. 985–988 & 1945–1948 (1990). The resulting compound (V) is reacted with a disubstituted phosphine oxide in the presence of palladium acetate, 1,3-bisdiphenylphosphinopropane (DPPP), and N,N-diisopropylethylamine to obtain a 2-disubstituted phosphinyl-2'-trifluoromethanesulfonyloxy-1,1'-binaphthyl (VI) in accordance with the method described in J. Org. Chem., Vol. 58, pp. 1945–1948 (1993). The compound (VI) is then reduced with, e.g., trichlorosilane to give a 2-disubstituted phosphino-2'-trifluoromethanesulfonyloxy-1,1'-binaphthyl (III).

Commercially available optically active 1,1'-bi-2-naphthol can be made use of as a starting compound (IV). Alternatively, it may be prepared with ease at high optical purity and in high yield by a known process disclosed, e.g., in J. Org. Chem., Vol. 53, p. 3607 (1988) and JP-A-64-13063, which comprises reacting optically active O,O'-dimethyl-N,N'-tetramethyltartaric acid amide obtainable from natural or unnatural tartaric acid with racemic binaphthol to form a complex between the acid amide and one of the optically active compounds of the racemic binaphthol, and resolving the complex.

The unsymmetric diphosphine compound (I) and the unsymmetric diphosphine monoxide compound (II) can be synthesized in accordance with, for example, the following reaction scheme B.

wherein $Ni(dppe)Cl_2$ represents [1,2-bis(diphenylphosphino)ethane]nickel dichloride; DABCO represents diazabicyclo[2,2,2]octane; and other symbols are as defined above.

A 2-disubstituted phosphino-2'-trifluoromethanesulfonyloxy-1,1'-binaphthyl (III) is reacted with a disubstituted phosphine oxide in the presence of a catalytic amount of a transition metal-phosphine complex to obtain a 2-disubstituted phosphino-2'-disubstituted phosphinyl-1,1'-binaphthyl (II) (unsymmetric diphosphine oxide compound).

The unsymmetric diphosphine oxide compound (II) is then reduced with a reducing agent, such as trichlorosilane, to obtain a 2,2'-bis(disubstituted phosphino)-1,1'-binaphthyl (I) (unsymmetric diphosphine compound).

The transition metal-phosphine complex which can be used in the preparation of the unsymmetric diphosphine compound (I) and unsymmetric diphosphine monoxide compound (II) includes those comprising cobalt or nickel as a transition metal. The phosphine ligand in the complex is not particularly limited and includes triphenylphosphine, tri-o-tolylphosphine, tri-p-tolylphosphine, tri-m-tolylphosphine, 1,2-bisdiphenylphosphinoethane, 1,3-bisdiphenylphosphinopropane, 1,4-bisdiphenylphosphinobutane, 1,5-bisdiphenylphosphinopentane, and 1,6-bisdiphenylphosphinohexane. While the reducing agent to be used in the preparation of the unsymmetric diphosphine compound (I) is not particularly limited, a silane compound is usually used. Suitable silane compounds include trichlorosilane, dichlorosilane, chlorosilane, methyldichlorosilane, dimethylchlorosilane, phenyldichlorosilane, phenylmethylchlorosilane, and diphenylchlorosilane.

The thus prepared novel unsymmetric diphosphine compound (I) serves as a ligand to provide a complex with a transition metal. The transition metals capable of forming a complex with the compound (I) include rhodium, ruthenium, iridium, palladium, and nickel.

The transition metal-unsymmetric diphosphine complex of the invention can be prepared by known processes as described below. In what follows, the symbols "L", "cod", and "nbd" stand for a diphosphine compound (I), 1,5-cyclooctadiene, and norbornadiene, respectively.

(1) Rhodium Complex

A rhodium complex can be prepared by reacting a 2,2'-bis(disubstituted phosphino)-1,1'-binaphthyl (I) with bis(cycloocta-1,5-diene)rhodium (I) tetrafluoroborate in accordance with the method described in The Chemical Society of Japan (ed.), *Dai 4-han Jikken Kagaku Koza*, Vol. 18, "Yuki Kinzoku Sakutai", pp. 339–344 published by Maruzen Co. (1991). Examples of rhodium complexes thus prepared are Rh(L)Cl, Rh(L)Br, Rh(L)I, [Rh(cod)(L)]$BF_4$, [Rh(cod)(L)]$ClO_4$, [Rh(cod)(L)]$PF_6$, [Rh(cod)(L)]$BPh_4$, [Rh(nbd)(L)]$BF_4$, [Rh(nbd)(L)]$ClO_4$, [Rh(nbd)(L)]$PF_6$, and [Rh(nbd)(L)]$BPh_4$, (wherein L represents a diphosphine compound (I) (hereinafter the same)).

(2) Ruthenium Complex

A ruthenium complex can be prepared by reacting a 2,2'-bis(disubstituted phosphino)-1,1'-binaphthyl (I) with [Ru(cod)$Cl_2$], under reflux by heating in toluene solvent in the presence of triethylamine in accordance with the method described in *J. Chem. Soc. Chem. Commun.*, p. 922 (1988). It can also be prepared by heating a 2,2'-bis(disubstituted phosphino)-1,1'-binaphthyl (I) and [Ru(p-cymene)$I_2$]$_2$ in methylene chloride and ethanol while stirring by heating in accordance with the method described in *J. Chem. Soc., Chem. Commun.*, p. 1208 (1989). Examples of ruthenium complexes thus prepared are Ru(OAc)$_2$(L), Ru$_2$Cl$_4$(L)$_2$N(C$_2$H$_5$)$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, and [Ru(L)](BPh$_4$)$_2$.

(3) Iridium Complex

An iridium complex can be prepared by reacting a 2,2'-bis(disubstituted phosphino)-1,1'-binaphthyl (I) and [Ir(cod)(CH$_3$CN)$_2$]BF$_4$ under stirring in tetrahydrofuran in accordance with the method of *J. Organomet. Chem.*, Vol. 428, p. 213 (1992). Examples of the iridium complexes thus prepared are Ir(L)Cl, Ir(L)Br, Ir(L)I, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]BF$_4$, [Ir(nbd)(L)]ClO$_4$, [Ir(nbd)(L)]PF$_6$, and [Ir(nbd)(L)]BPh$_4$.

(4) Palladium Complex

A palladium complex can be prepared by reacting a 2,2'-bis(disubstituted phosphino)-1,1'-binaphthyl (I) and a π-allylpalladium chloride in accordance with the method described in *J. Am. Chem. Soc.*, Vol. 113, p. 9887 (1991). Examples of palladium complexes thus prepared are PdCl$_2$(L), (π-allyl)Pd(L), [Pd(L)]BF$_4$, [Pd(L)]ClO$_4$, [Pd(L)]PF$_6$, and [Pd(L)]BPh$_4$.

(5) Nickel Complex

A nickel complex can be prepared by dissolving a 2,2'-bis(disubstituted phosphino)-1,1'-binaphthyl (I) and nickel chloride in a mixed solvent of isopropyl alcohol and methanol and heating the solution with stirring in accordance with the method described in The Chemical Society of Japan (ed.), *Dai 4-han Jikken Kagaku Koza*, Vol. 18, "Yuki Kinzoku Sakutai", p. 376, published by Maruzen Co. (1991). Examples of nickel catalysts thus prepared are NiCl$_2$(L), NiBr$_2$(L), NiI$_2$(L), [Ni(L)](BF$_4$)$_2$, [Ni(L)](ClO$_4$)$_2$, [Ni(L)](PF$_6$)$_2$, and [Ni(L)](BPh$_4$)$_2$.

The transition metal-unsymmetric diphosphine compound complexes thus prepared can be used as a catalyst for asymmetric synthesis, for example, asymmetric hydrogenation and asymmetric hydrosilylation, to give a product of desired absolute configuration with a high optical purity.

For example, asymmetric hydrogenation of a ketone in the presence of a combination of the unsymmetric diphosphine compound (I) and a complex precursor, i.e., a metal complex before addition of a ligand (e.g., [Ru(p-cymene)I$_2$]$_2$ for a ruthenium complex, [Ir(cod)(CH$_3$CN)$_2$]BF$_4$ for an iridium complex, [(π-allyl)PdCl]$_2$ for a palladium complex, or NiCl$_2$ for a nickel complex), or in the presence of the transition metal complex of the invention gives a corresponding optically active alcohol. This reaction is carried out by dissolving the substrate ketone in an appropriate solvent, such as methanol, tetrahydrofuran, methylene chloride, benzene or a mixture thereof, adding the complex of the invention in an amount of 1/1000 to 1/10 mol per mole of the substrate, and keeping the reaction system at 10° to 50° C. at a hydrogen pressure of 2 to 100 kg/cm².

Thus, the invention provides a novel unsymmetric diphosphine compound, 2,2'-bis(disubstituted phosphino)-1,1'-binaphthyl compound. The unsymmetric diphosphine compound of the invention is capable of forming a complex with a transition metal, such as rhodium, ruthenium, iridium, palladium or nickel. The resulting transition metal complex catalyzes various asymmetric synthesis reactions, such as asymmetric hydrogenation and asymmetric hydrosilylation, exhibiting excellent performance in selectivity, conversions, and catalytic activity, to provide a product of desired absolute configuration at high optical purity and in high yield.

The present invention will now be illustrated in greater detail with reference to Examples, but it should be understood that the invention is not deemed to be limited thereto. (Unless otherwise indicated, all the percents are by weight.)

Equipment and instruments used for measuring physical properties of the products prepared are as follows.

NMR: Model AM-400 (manufactured by Bruker Inc.) $^1$H-NMR: 400 MHz, tetramethylsilane (internal standard) $^{31}$P-NMR: 162 MHz, 85% phosphoric acid (outer standard) Melting Point: Model MP-500D (manufactured by Yanaco Co.) Optical Rotation: Model DIP-4 (manufactured by JASCO Inc.) GLC: Model 5890-II (manufactured by Hewlett Packard) HPLC: LC10AT, SPD10A (manufactured by Shimadzu Corp.) Mass Spectrum: M-80B (manufactured by Hitachi, Ltd.)

EXAMPLE 1

(1) Synthesis of (S)-2,2'-Bis(trifluoromethanesulfonyloxy)-1,1'-binaphthyl (V)

In 181 ml of methylene chloride were dissolved 36.2 g (127 mmol) of (S)-1,1'-bi-2-naphthol and 25.2 g (319 mmol) of pyridine, and the solution was cooled to 0° C. To the solution was added dropwise 76.5 ml (271 mmol) of trifluoromethanesulfonic acid anhydride, followed by stirring at room temperature for 18 hours. The reaction mixture was washed with 200 ml of a 2N hydrochloric acid aqueous solution. The organic layer was washed with water and then with a sodium chloride aqueous solution, and the solvent was removed by evaporation to give 69.3 g of a crude product. Recrystallization from 280 ml of hexane gave 64.1 g (yield: 92%) of the title compound.

$^1$H-NMR (CDCl$_3$) δ ppm: 7.25–8.15 (m, aromatic proton)

(2) Synthesis of (S)-2-Di(2-naphthyl)phosphinyl-2'-(trifluoromethanesulfonyloxy)-1,1'-binaphthyl (VI)

In 45 ml of dimethyl sulfoxide (DMSO) were dissolved 9.1 g (16.5 mmol) of (S)-2,2'-bis (trifluoromethanesulfonyloxy)-1,1'-binaphthyl, 0.372 g (1.65 mmol) of palladium acetate, 0.683 g (1.65 mmol) of 1,3-bis(diphenylphosphino)propane, and 0.113 g (1.65 mmol) of sodium formate, and the solution was stirred at room temperature for 1.5 hours. To the solution was added a solution of 6.00 g (19.8 mmol) of di(2-naphthyl)phosphine oxide and 5.8 ml (33 mmol) of N,N'-diisopropylethylamine in 55 ml of DMSO, followed by stirring at 100° C. for 4 hours. The reaction mixture was cooled to room temperature, and 75 ml of methylene chloride was added thereto. The solution was cooled on an ice bath, and 100 ml of a 2N hydrochloric acid aqueous solution was slowly added thereto dropwise. After stirring at room temperature for 30 minutes, the mixture was allowed to stand for liquid-liquid separation. The aqueous layer was extracted with methylene chloride. The combined organic layer was washed with water and dried over magnesium sulfate. The solvent was removed by concentration, and the residue was purified by silica gel column chromatography (hexane:ethyl acetate=4:1 to 1:4 by volume) to obtain 8.45 g (75.3%) of the title compound as yellowish white crystals.

Melting point: 122°–123° C. Optical rotation: $[\alpha]_D^{24}$ –66.8° (c=1.00, toluene) $^1$H-NMR (CDCl$_3$) δ ppm: 6.99–8.05 (m, aromatic proton) $^{31}$P-NMR (CDCl$_3$) δ ppm: 29.03 Mass spectrum (m/z): 703 [(M+H)$^+$]

(3) Synthesis of (S)-2-Di(2-naphthyl)phosphino-2'-(trifluoromethanesulfonyloxy)-1,1'-binaphthyl (III)

Trichlorosilane (3.7 ml, 37 mmol) was added to a mixture of 8.59 g (12.2 mmol) of (S)-2-di(2-naphthyl)phosphinyl-2'-(trifluoromethanesulfonyloxy)-1,1'-binaphthyl, 170 ml of toluene, and 4.6 ml (36 mmol) of dimethylaniline, and the mixture was stirred at 90° C. for 1 hours and then under reflux for 22 hours. The reaction mixture was cooled, and 150 ml of a 1N sodium hydroxide aqueous solution was slowly added thereto dropwise. The aqueous layer was extracted with 50 ml of toluene. The combined organic layer was washed successively with 150 ml of water, 150 ml of a 1N hydrochloric acid aqueous solution, and two 150 ml portions of water. The organic layer was concentrated, and the residue was purified by silica gel column chromatography (hexane:ethyl acetate=1:0 to 9:1 by volume) to obtain 7.00 g (83.9%) of the title compound as a yellow solid.

Melting point: 113°–115° C. Optical rotation: $[\alpha]_D^{24}$ +3.9° (c=1.00, ethanol) $^1$H-NMR (CDCl$_3$) δ ppm: 6.86–8.07 (m, aromatic proton) $^{31}$P-NMR (CDCl$_3$) δ ppm: –10.95 Mass spectrum (m/z): 686 (M$^+$)

(4) Synthesis of (S)-2-Di(2-naphthyl)phosphino-2'-diphenylphosphinyl-1,1-binaphthyl (II)

In 4 ml of dimethylformamide (DMF) were dissolved 1.00 g (1.46 mmol) of (S)-2-di(2-naphthyl)phosphino-2'-(trifluoromethanesulfonyloxy)-1,1'-binaphthyl, 0.327 g (2.91 mmol) of diazabicyclo[2,2,2]octane (DABCO), and 76.9 mg (0.146 mmol) of [1,2-bis(diphenylphosphino)ethane]nickel dichloride (Ni(dppe)Cl$_2$), and the solution was stirred at room temperature for 1 hour. To the solution was added a solution of 0.357 g (1.77 mmol) of diphenylphosphine oxide in 2.4 ml of DMF. The mixture was stirred at 100° C. for 16 hours, followed by concentration. To the residue was added 10 ml of methylene chloride, and the solution was washed successively with 10 ml of water and 10 ml of a 1N hydrochloric acid aqueous solution. The solution was concentrated, and the residue was purified by silica gel column chromatography (hexane:ethyl acetate=1:0 to 0:1 by volume) to give 0.59 g (56.2%) of the title compound as a yellowish white solid.

Melting point: 242°–245° C. Optical rotation: $[\alpha]_D^{26}$ –80.4° (c=1.00, chloroform) $^{31}$P-NMR (CDCl$_3$) δ ppm: –13.09, +28.21 Mass spectrum (m/z): 738 (M$^+$)

(5) Synthesis of (S)-2-Di(2'-naphthyl)phosphino-2'-diphenylphosphino-1,1'-binaphthyl (I)

Trichlorosilane (0.3 ml, 3.6 mmol) was added to a mixture of 0.535 g (0.723 mmol) of (S)-2-di(2-naphthyl)phosphino-2'-diphenylphosphinyl-1,1'-binaphthyl, 0.46 ml (3.6 mmol) of dimethylaniline, and 11 ml of toluene, and the mixture was stirred at 90° C. for 1 hour and then under reflux for 24 hours. The reaction mixture was cooled on an ice bath, and 21 ml of a 1N sodium hydroxide aqueous solution was added thereto. The aqueous layer was extracted with toluene, and the organic layer was washed successively with 10 ml of water, 21 ml of a 1N hydrochloric acid aqueous solution, and two 10 ml portions of water. The solution was concentrated, and the residue was purified by silica gel column chromatography (hexane:ethyl acetate=1:0 to 1:1 by volume) to afford 0.426 g (81.2%) of the title compound as a white solid.

Melting point: 140°–143° C. Optical rotation: $[\alpha]_D^{26}$ –190.41° (c=0.50, toluene) $^{31}$P-NMR (CDCl$_3$) δ ppm: –14.73 (d, J=10.5 Hz), –13.43 (d, J=10.5 Hz) Mass spectrum (m/z): 722 (M$^+$)

EXAMPLE 2

(1) Synthesis of (R)-2-Diphenylphosphinyl-2'-(trifluoromethanesulfonyloxy)-1,1'-binaphthyl (VI)

In 100 ml of DMSO were dissolved 11 g (20 mmol) of (R)-2,2'-bis(trifluoromethanesulfonyloxy)-1,1'-binaphthyl, 0.255 g (50 mol %) of palladium acetate, and 0.43 g (50 mol %) of 1,4-bis(diphenylphosphino)propane, and the solution was stirred at room temperature for 1.5 hours. To the solution was added a solution of 8.08 g (40 mmol) of diphenylphosphine oxide and 20 ml of N,N'-diisopropylethylamine in 100 ml of DMSO, followed by stirring at 100° C. for 12 hours. The reaction mixture was cooled to room temperature, and 75 ml of methylene chloride was added thereto. The solution was cooled on an ice bath, and 100 ml of a 2N hydrochloric acid aqueous solution was slowly added thereto dropwise. After stirring at room temperature for 30 minutes, the mixture was allowed to stand for liquid-liquid separation. The aqueous layer was extracted with methylene chloride. The combined organic layer was washed with water and dried over magnesium sulfate. The solvent was removed by concentration, and the residue was purified by silica gel column chromatography (hexane:ethyl acetate=4:1 to 1:4 by volume) to obtain 11.5 q (96%) of the title compound as yellowish white crystals.

Optical rotation: $[\alpha]_D^{24}$ +44.45° (c=0.50, chloroform) $^1$H-NMR (CDCl$_3$) δ ppm: 7.00–8.01 (d, m, aromatic proton) $^{31}$P-NMR (CDCl$_3$) δ ppm: 28.73

(2) Synthesis of (R)-2-Diphenylphosphino-2'-(trifluoromethanesulfonyloxy)-1,1'-binaphthyl (III)

Trichlorosilane (2.5 ml, 25 mmol) was added to a mixture of 11.5 g (19.2 mmol) of (R)-2-diphenylphosphinyl-2'-(trifluoromethanesulfonyloxy)-1,1'-binaphthyl, 170 ml of toluene, and 3.1 ml (24 mmol) of dimethylaniline, and the mixture was stirred at 90° C. for 1 hour and then under reflux for 7 hours. The reaction mixture was cooled, and 150 ml of a 1N sodium hydroxide aqueous solution was slowly added thereto dropwise. The aqueous layer was extracted with 50 ml of toluene, and the combined organic layer was washed successively with 150 ml of water, 150 ml of a 1N hydrochloric acid aqueous solution, and two 150 ml portions of water. The organic layer was concentrated, and the residue was purified by silica gel column chromatography (hexane:ethyl acetate=1:0 to 9:1 by volume) to afford 9.03 g (80%) of the title compound as a yellow solid.

Melting point: 55°–58° C. Optical rotation: $[\alpha]_D^{24}$ −110.6° (c=0.85, methylene chloride) $^1$H-NMR (CDCl$_3$) δ ppm: 6.63–8.20 (m, aromatic proton) $^{31}$P-NMR (CDCl$_3$) δ ppm: +30.80

(3) Synthesis of (R)-2-Diphenylphosphino-2'-di(p-trifluoromethylphenyl)phosphino-1,1'-binaphthyl (I)

A mixture of 0.99 g (1.63 mmol) of (R)-2-diphenylphosphino-2'-(trifluoromethanesulfonyloxy)-1,1'-binaphthyl, 179.4 mg (0.340 mmol) of [1,2-bis(diphenylphosphino)ethane]nickel dichloride, 875.0 mg (7.02 mmol) of DABCO, and 4 ml of DMF was stirred at room temperature for 1 hour in a nitrogen stream. A solution of 2.18 g (6.45 mmol) of di(p-trifluoromethylphenyl)phosphine oxide in 14 ml of DMF was added thereto, followed by stirring at 100° C. for 25 hours. The solvent was removed by evaporation under reduced pressure, and the residue was dissolved in 50 ml of dichloromethane. The organic layer was washed successively with 20 ml of water and 20 ml of a 1N hydrochloric acid aqueous solution, and dried over anhydrous sodium sulfate. The solvent was removed by evaporation under reduced pressure, and the residue was purified by silica gel column chromatography (hexane:ethyl acetate=15:1 by volume) to yield 0.49 g (37%) of the title compound.

Melting point: 110°–112° C. Optical rotation: $[\alpha]_D^{24}$ +69.1° (c=0.50, chloroform) $^1$H-NMR (CDCl$_3$) δ ppm: 6.77–7.93 (m) $^{31}$P-NMR (CDCl$_3$) δ ppm: −14.5, −14.7 Mass spectrum (m/z): 759 (M$^+$)

EXAMPLES 3 TO 6

Unsymmetric diphosphine monoxide compounds (II) shown in Table 1 below were prepared in the same manner as in Examples 1 and 2.

TABLE 1

| Example No. | Ar$^1$ | Ar$^2$ | Physical Properties |
|---|---|---|---|
| 3 | phenyl | p-tolyl | m.p. 143–150° C.<br>$[\alpha]_D^{24}$ +32.4° (c = 0.500, CHCl$_3$)<br>$^{31}$P-NMR (CDCl$_3$) δ: +27.9, −14.6<br>Mass spectrum: 667 (M$^+$) |
| 4 | phenyl | biphenyl | m.p. 245–250° C.<br>$[\alpha]_D^{24}$ +2.40° (c = 0.500, CHCl$_3$)<br>$^{31}$P-NMR (CDCl$_3$) δ: +27.7, −14.7<br>Mass spectrum: 791 (M$^+$) |
| 5 | phenyl | p-fluoro-phenyl | m.p. 130–135° C.<br>$[\alpha]_D^{24}$ +66.2° (c = 0.501, CHCl$_3$)<br>$^{31}$P-NMR (CDCl$_3$) δ: +26.5, −14.6<br>Mass spectrum: 675 (M$^+$) |
| 6 | phenyl | 2-thienyl | m.p. 249–252° C.<br>$[\alpha]_D^{24}$ +0.59° (c = 1.01, CHCl$_3$)<br>$^{31}$P-NMR (CDCl$_3$) δ: +13.6, −14.7<br>Mass spectrum: 650 (M$^+$) |

EXAMPLES 7 TO 10

Unsymmetric diphosphine compounds (I) shown in Table 2 below were prepared in the same manner as in Examples 1 and 2.

TABLE 2

| Example No. | Ar$^1$ | Ar$^2$ | Physical Properties |
|---|---|---|---|
| 7 | phenyl | p-tolyl | m.p. 207–209° C.<br>$[\alpha]_D^{24}$ +86.36° (c = 0.506, CHCl$_3$)<br>$^{31}$P-NMR (CDCl$_3$) δ: −16.4, −14.8<br>Mass spectrum: 651 (M$^+$) |
| 8 | phenyl | biphenyl | m.p. 278–281° C.<br>$[\alpha]_D^{24}$ +12.49° (c = 0.512, CHCl$_3$)<br>$^{31}$P-NMR (CDCl$_3$) δ: −15.8, −14.7<br>Mass spectrum: 775 (M$^+$) |
| 9 | phenyl | p-fluoro-phenyl | m.p. 271–272° C.<br>$[\alpha]_D^{24}$ +1.99° (c = 0.502, CHCl$_3$)<br>$^{31}$P-NMR (CDCl$_3$) δ: −16.9, −14.6<br>Mass spectrum: 659 (M$^+$) |
| 10 | phenyl | 2-thienyl | m.p. 185–188° C.<br>$[\alpha]_D^{24}$ +170.74° (c = 1.08, CHCl$_3$)<br>$^{31}$P-NMR (CDCl$_3$) δ: −41.0, −14.4<br>Mass spectrum: 634 (M$^+$) |

EXAMPLES 11 TO 16

Ruthenium complexes and rhodium complexes were prepared by using the unsymmetric diphosphine compounds (I) obtained in Examples 1, 2, and 7 to 10 as ligands. The NMR data of the resulting complexes are shown in Table 3 below.

(1) Synthesis of Ruthenium Complex

In a mixed solvent of 6 ml of methylene chloride and 3 ml of ethanol were dissolved 48.9 mg (0.05 mmol) of [Ru(p-cymene)I$_2$]$_2$ and 0.1 mmol of the unsymmetric diphosphine compound (I). The solution was stirred at 50° C. for 3 hours and then concentrated to obtain a ruthenium complex.

(2) Synthesis of Rhodium Complex

In a mixed solvent of 5 ml of tetrahydrofuran and 5 ml of methylene chloride were dissolved 40.5 mg (0.1 mmol) of [Rh(cod)$_2$]BF$_4$ and 0.1 mmol of the unsymmetric diphosphine compound (I). The solution was stirred at room temperature for 2 hours and then concentrated to obtain a rhodium complex.

TABLE 3

| Example No. | Ligand | Ruthenium Complex | Rhodium Complex |
|---|---|---|---|
| 11 | Compound of Example 1 | [RuI(p-cymeme) (L*)]I; $^{31}$P-NMR (CDCl$_3$) δ ppm: 25.1 (d, J = 60), 41.8 (d) | [Rh(cod)(L)]BF$_4$; $^{31}$P-NMR (CDCl$_3$) δ ppm: 24.8 (dd, J = 147.8, 31.8Hz), 28.3 (dd, J = 144.2, 31.8Hz) |
| 12 | Compound of Example 2 | [RuI(p-cymene)(L)]I; $^{31}$P-NMR (CDCl$_3$) δ ppm: 42.0 (d, J = 59), 40.8 (d, J = 60), 26.4 (d, J = 61), 24.1 (d, J = 60) | [Rh(cod)(L)]BF$_4$; $^{31}$P-NMR (CDCl$_3$) δ ppm: 24.0 (dd, J = 143.8, 21.9Hz), 28.6 (dd, J = 146.2, 21.9Hz) |
| 13 | Compound of Example 7 | [RuI(p-cymene)(L)]I; $^{31}$P-NMR (CDCl$_3$) δ ppm: 41.6 (d, J = 70), 39.7 (d, J = 53), 24.9 (d, J = 76), 23.2 (d, J = 60) | [Rh(cod)(L)]BF$_4$; $^{31}$P-NMR (CDCl$_3$) δ ppm: 23.9 (dd, J = 145.5, 32.3Hz), 26.9 (dd, J = 146.1, 32.4Hz) |
| 14 | Compound of Example 8 | [RuI(p-cymene)(L)]I; $^{31}$P-NMR (CDCl$_3$) δ ppm: 41.7 (d, J = 58), 40.2 (d, J = 60), 24.8 (d, J = 48), 23.3 (d, J = 59) | [Rh(cod)(L)]BF$_4$; $^{31}$P-NMR (CDCl$_3$) δ ppm: 25.3 (dd, J = 146.0, 32.3Hz), 25.9 (dd, J = 146.3, 32.3Hz) |
| 15 | Compound of Example 9 | [RuI(p-cymene)(L)]I; $^{31}$P-NMR (CDCl$_3$) δ ppm: 41.5 (d, J = 60), 39.5 (d, J = 60), 24.5 (d, J = 60), 23.7 (d, J = 62) | [Rh(cod)(L)]BF$_4$; $^{31}$P-NMR (CDCl$_3$) δ ppm: 23.9 (dd, J = 147.8, 32.5Hz), 25.6 (dd, J = 146.0, 32.8Hz) |
| 16 | Compound of Example 10 | [RuI(p-cymene)(L)]I; $^{31}$P-NMR (CDCl$_3$) δ ppm: 4.5 (d, J = 66), 12.2 (d, J = 63), 24.2 (d, J = 52.8), 42.4 (d, J = 65) | [Rh(cod)(L)]BF$_4$; $^{31}$P-NMR (CDCl$_3$) δ ppm: 4.2 (dd, J = 147.5, 31.5Hz), 23.9 (dd, J = 145.7, 31.5Hz) |

*"L" represents a diphosphine compound represented by formula (I).

APPLICATION EXAMPLE

Hydrogenation of Ketopantolactone

A mixture of 86 mg (0.11 mmol) of (S)-2-di(2-naphthyl)phosphino-2'-diphenylphosphino-1,1'-binaphthyl, 28 mg (0.1 mmol) of [Ru(cod)Cl$_2$]$_n$, 3 ml of toluene, and 0.05 ml (0.4 mmol) of triethylamine was heated under reflux for 16 hours in a nitrogen stream. The solvent was removed by evaporation, and the residue was dried to solid under reduced pressure.

In a stainless steel-made autoclave were charged 9.5 mg (0.01 mmol) of the resulting catalyst Ru$_2$Cl$_4$·{(S)-di(2-naphthyl)phosphino-2'-diphenylphosphino-1,1'-binaphthyl}$_2$·triethylamine, 250 mg (2 mmol) of Ketopantolactone (dihydro-4,4-dimethyl-2,3-furandione, produced by Aldrich Co.), 2.5 ml of isopropyl alcohol, and 6.5 mg (0.1 mmol) of potassium hydroxide, and the mixture was stirred at 50° C. and 50 atm for 16 hours. The reaction mixture was concentrated, and the residue was purified by silica gel column chromatography (hexane:ethyl acetate=3:1 to 1:1 by volume).

The resulting hydrogenation product (25 mg) was stirred with 150 mg of (S)-α-methoxy-α-trifluoromethylphenylacetyl chloride and 0.5 ml of pyridine to be converted to an (S)-α-methoxy-α-trifluoromethylphenylacetate, which was then analyzed by HPLC under the following conditions. As a result, the optical purity of the product was found to be 50% ee.

HPLC Column: Inertsil (produced by GL Science) SIL 5 μm, 4.6×250 mm Eluent: hexane:tetrahydrofuran=95:5 by volume Flow rate: 1 ml/min Detection: UV (254 nm)

While the invention has been described in detail and with reference to specific examples thereof, it will be apparent to one skilled in the art that various changes and modifications can be made therein without departing from the spirit and scope thereof.

What is claimed is:

1. An unsymmetric diphosphine monoxide compound represented by formula (II):

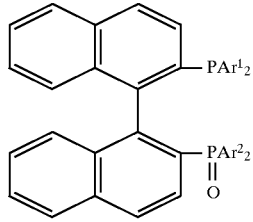

(II)

wherein Ar$^1$ and Ar$^2$, which are different from each other, each represent a phenyl group, a phenyl group substituted with 1 to 5 groups arbitrarily selected from the group consisting of a halogen atom, a lower alkyl group, a lower alkoxy group, a di(lower alkyl)amino group, a halogenated lower alkyl group, and a phenyl group, a naphthyl group, a naphthyl group substituted with a lower alkyl group or a lower alkoxy group, a pyridyl group, a quinolyl group, an isoquinolyl group, a furfuryl group, a benzofurfuryl group, a thienyl group, or a benzothienyl group.

2. A process for preparing an unsymmetric diphosphine compound represented by formula (I):

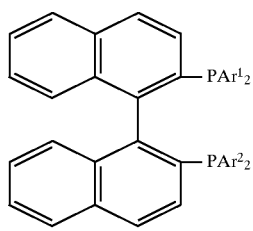

(I)

wherein Ar$^1$ and Ar$^2$, which are different from each other, each represent a phenyl group, a phenyl group substituted with 1 to 5 groups arbitrarily selected from the group consisting of a halogen atom, a lower alkyl group, a lower alkoxy group, a di(lower alkyl)amino group, a halogenated lower alkyl group, and a phenyl group, a naphthyl group, a naphthyl group substituted with a lower alkyl group or a lower alkoxy group, a pyridyl group, a quinolyl group, an isoquinolyl group, a furfuryl group, a benzofurfuryl group, a thienyl group, or a benzothienyl group,
comprising reacting a 2-disubstituted phosphino-2'-trifluoromethanesulfonyloxy-1,1'-binaphthyl represented by formula (III):

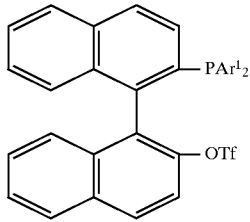

(III)

wherein $Ar^1$ is as defined above; and Tf represents a trifluoromethanesulfonyl group,
with a disubstituted phosphine oxide represented by formula (IV):

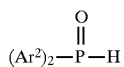

(IV)

wherein $Ar^2$ is as defined above, provided that $Ar^2$ and $Ar^1$ are not the same, in the presence of a transition metal-phosphine complex to form an unsymmetric diphosphine monoxide compound represented by formula (II):

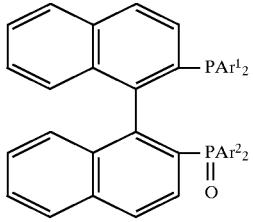

(II)

wherein $Ar^1$ and $Ar^2$ are as defined above, provided that $Ar^1$ and $Ar^2$ are not the same, and reducing the compound represented by formula (II).

* * * * *